United States Patent
Chen et al.

(10) Patent No.: US 10,669,309 B2
(45) Date of Patent: Jun. 2, 2020

(54) METHOD FOR EXTRACTING EPSILON-POLYLYSINE AND ITS HYDROCHLORIDE SALT FROM FERMENTATION BROTH

(71) Applicant: Jiangnan University, Wuxi (CN)

(72) Inventors: Xusheng Chen, Wuxi (CN); Zhonggui Mao, Wuxi (CN); Jianhua Zhang, Wuxi (CN); Hongjian Zhang, Wuxi (CN); Ke Wang, Wuxi (CN); Honggang He, Wuxi (CN)

(73) Assignee: Jiangnan University, Wuxi, Jiangsu (CN)

( * ) Notice: Subject to any disclaimer, the term of this patent is extended or adjusted under 35 U.S.C. 154(b) by 0 days.

(21) Appl. No.: 15/677,023

(22) Filed: Aug. 15, 2017

(65) Prior Publication Data
US 2018/0127462 A1 May 10, 2018

(30) Foreign Application Priority Data
Nov. 4, 2016 (CN) .......................... 2016 1 0961477

(51) Int. Cl.
| | |
|---|---|
| *C07K 1/36* | (2006.01) |
| *B01D 61/58* | (2006.01) |
| *C08G 69/10* | (2006.01) |
| *B01J 41/05* | (2017.01) |
| *B01J 39/07* | (2017.01) |
| *B01D 15/36* | (2006.01) |
| *B01J 41/07* | (2017.01) |
| *B01J 39/05* | (2017.01) |
| *B01D 21/26* | (2006.01) |
| *B01D 61/02* | (2006.01) |
| *B01D 61/14* | (2006.01) |
| *C07K 1/18* | (2006.01) |
| *C07K 1/34* | (2006.01) |
| *C07K 14/36* | (2006.01) |
| *B01D 63/06* | (2006.01) |

(52) U.S. Cl.
CPC .............. *C07K 1/36* (2013.01); *B01D 15/362* (2013.01); *B01D 15/363* (2013.01); *B01D 21/262* (2013.01); *B01D 61/027* (2013.01); *B01D 61/145* (2013.01); *B01D 61/58* (2013.01); *B01J 39/05* (2017.01); *B01J 39/07* (2017.01); *B01J 41/05* (2017.01); *B01J 41/07* (2017.01); *C07K 1/18* (2013.01); *C07K 1/34* (2013.01); *C07K 14/36* (2013.01); *C08G 69/10* (2013.01); *B01D 63/06* (2013.01); *B01D 2311/04* (2013.01); *B01D 2311/06* (2013.01); *B01D 2311/2623* (2013.01)

(58) Field of Classification Search
None
See application file for complete search history.

(56) References Cited

FOREIGN PATENT DOCUMENTS

| CN | 103194500 A | * | 7/2013 | |
| EP | 0507591 A2 | * | 10/1992 | .......... B01D 15/363 |

OTHER PUBLICATIONS

Chen et al. "Separation and purification of epsilon-poly-L-lysine from fermentation broth" Process Biochemistry 51:134-141. (Year: 2015).*
Saraswat et al. "Preparative Purification of Recombinant Proteins: Current Status and Future Trends" BioMed Research International, vol. 2013, Article ID 312709. (Year: 2013).*
Wang et al. "Genome Shuffling and Gentamicin-Resistance to Improve Epsilon-Poly-L-Lysine Productivity of Streptomyces albulus W-156" Appl. Biochem. Biotechnol. 180:1601-1617 (Year: 2016).*
Bandar et al. "Purification and characterization of poly-epsilon-lysine from Streptomcyes noursei NRRL 5126" J. Scientific & Industrial Research 73:33-40. (Year: 2014).*
GE Healthcare "Ion exchange colums and media Selection Guide" (Year: 2008).*

* cited by examiner

*Primary Examiner* — Christina Bradley
(74) *Attorney, Agent, or Firm* — IPro, PLLC; Na Xu

(57) ABSTRACT

The present invention provides a method for extracting ε-polylysine (ε-PL) and its hydrochloride salt from fermentation broth, which belongs to the field of bio-separation engineering. ε-PL and its hydrochloride salt are produced from fermentation broth through sequential solid-liquid separation, ultrafiltration, two-stage ion exchange, nanofiltration, evaporation concentration and drying techniques. Technologies of membrane filtration and two-stage ion exchange are applied to the preparation of ε-PL and its hydrochloride salt in the present invention, and the invention are characterized by reduced cost, improved automation, and increased product yield and purity, and the method of the present invention would be more suitable for industrial production.

6 Claims, 2 Drawing Sheets

METHOD FOR EXTRACTING EPSILON-POLYLYSINE AND ITS HYDROCHLORIDE SALT FROM FERMENTATION BROTH

CROSS-REFERENCES AND RELATED APPLICATIONS

This application claims the benefit of priority to Chinese Application No. 201610961477.5, "A method for extracting ε-polylysine and its hydrochloride salt from fermentation broth", filed Nov. 4, 2016, which is herein incorporated by reference in its entirety.

BACKGROUND OF THE INVENTION

Field of the Invention

The present invention relates to the field of bio-separation engineering, and more particularly relates to a method for extracting ε-polylysine and its hydrochloride salt from fermentation broth.

Description of the Related Art

ε-polylysine (ε-PL) is a kind of homo-poly-amino acid secreted by microorganism, such as *Streptomyces*, filamentous fungus or *Bacillus*. ε-PL is typically formed through the dehydration condensation reaction between α-COOH and ε-NH$_2$ of 25~35 L-lysine monomers, and its molecular weight is usually 2500-4500 Da. Because of a good aqueous solubility, strong thermal stability and a broad antibacterial spectrum, ε-PL is mainly used as a biological preservative in food industry of Japan, South Korea, Europe and the United States and other countries and regions. In 2014, China also approved the application of ε-PL and its hydrochloride salt in food industry of fruits & vegetables, rice & flour products, meat products, condiments, beverages and baking products. In fact, ε-PL is an obvious complementary in the antibacterial spectrum and range of application with, Nisin and Natamycin, which are already commonly used in the food industry as a biological preservative. Therefore, it is of great meaning to develop and market the applications of ε-PL and its hydrochloride salt in the food industry, which could solve the food safety problems caused by current chemical-food preservative.

The preparation of ε-PL and its hydrochloride salt is completely depended on separation, extraction and purification from fermentation broth of *Streptomycete*, and the costs of separation and extraction account for 70-80% of overall production costs. Obviously, the separation and extraction techniques could make significant contributions to achieve low cost. However, the already published methods of ε-PL separation and extraction mainly focused on research and development of the separation techniques unit, such as solid-liquid separation, ion-exchange adsorption and elution, product decolorization. Only little reports related to integral extraction process of ε-PL.

In fact, the variation of material property determines the methods of separation and extraction. For example, for the fermentation broth containing only 20-30 g·L$^{-1}$ ε-PL and 30 g·L$^{-1}$ dry-weight cell (Bioresource Technology, 2015, 187: 70-76; ZL200910069817.5), 70-80% yield and 95-97% purity of ε-PL can be realized by using the methods described in the patent ZL201110053004.2 and ZL200910152931.2. However, it is impossible to achieve effective biomass separation from fermentation broth (54.7 g·L$^{-1}$ ε-PL and 76.35 g·L$^{-1}$ dry-weight cell) of the Patent application CN201510021744.6 using the methods described, and the purity and yield of ε-PL were only about 60% and 50-60%, respectively. Therefore, the already published separation and extraction methods of ε-PL are only applicable to fermentation broth containing low ε-PL concentration and low biomass, rather than fermentation broth containing high ε-PL concentration and high biomass. And this is mainly because high ε-PL concentration in the fermentation broth usually associate with higher biomass, much more metabolic byproducts and more complex liquid properties. However, high-ε-PL concentration fermentation is the primary mean to improve fermentation efficiency and reduce production cost. Therefore, research and development of the separation and extraction technologies of ε-PL from fermentation broth containing high-ε-PL concentration and high biomass is the fundamental task to achieve low cost and high efficiency ε-PL biomanufacture.

DETAILED DESCRIPTION

To solve the problem, the present invention provides a method for efficient extraction of ε-PL and its hydrochloride salt from the fermentation broth.

In one embodiment of the present invention, the method described in the present invention comprising the following steps:

(1) Solid-liquid separation of fermentation broth: After flocculation or dilution, the fermentation broth is filtrated or centrifugated to remove the mycelia and water-insoluble impurities, and a clear fermentation broth supernatant is obtained;

(2) Ultrafiltration: an ultrafiltration membrane system is used to remove the water-soluble macromolecular impurities and water-insoluble impurities in the fermentation broth supernatant, and the ultrafiltration permeate is collected;

(3) Ion-exchange: the ultrafiltration permeate is pressured into the primary ion exchange column for adsorption until the resin is saturated; then, a detergent is used to remove impurities, and an elution reagent is used to desorb; the eluents are collected from the primary ion exchange column, and then forced into a secondary ion exchange column, and the final effluent liquid is collect;

(4) Nanofiltration: nanofiltration membrane system is used to desalt and concentrate the effluent liquid obtained from the step (3), and nanofiltration concentrate is collected;

(5) Bleaching: the collected nanofiltration concentrate is decolorated to obtain the decolorated liquid;

(6) Concentration: the decolorated liquid obtained from the step (5) is concentrated to a ε-polylysine content of 10-30%;

(7) Drying: the concentrate obtained from the step (6) is dried, to obtain the ε-polylysine and its hydrochloride salt product.

In one embodiment of the present invention, said fermentation broth is obtained by fermentation of *Streptomyces albulus* CGMCC NO. 10480.

In one embodiment of the present invention, said fermentation broth contains over 50 g·L$^{-1}$ ε-PL and over 60 g·L$^{-1}$ dry-weight cell.

In one embodiment of the present invention, said fermentation broth is prepared in accordance with the method described in the patent application CN 201510021744.6.

In one embodiment of the present invention, said fermentation broth is prepared by the following steps: *Streptomyces albulus* CGMCC NO. 10480 was inoculated into the fermentation medium with 6%-8% inoculum volume, the fermentation process was controlled with the stirring speed 200-800 rpm, temperature 28-32° C., ventilation 0.5-2 vvm, dissolved oxygen 28-32%; When pH dropped spontaneously to 4.5-5.2 at the first time, the fermentation pH was maintained at 4.8-5.2 for 10-15 h, then the pH was regulated to 2.8-3.2 and maintained for 22-26 h, finally the pH was adjust to 4.2-4.8 and maintained until the end of fermentation; when glycerol or glucose concentration in the fermentation broth dropped to less than 10 g·L$^{-1}$, glycerol or glucose solution was fed to maintain the concentration of glycerol or glucose at 9.5-10.5 g·L$^{-1}$; when $NH_4^+$-N concentration in the fermentation broth dropped to 1 g·L$^{-1}$ or less, the $NH_4^+$-N concentration was maintained at 0.8-1.2 g·L$^{-1}$ by feeding ammonium sulfate solution.

In one embodiment of present invention, said fermentation medium contains the following components (g·L$^{-1}$): glucose or glycerol 83, $(NH_4)_2SO_4$ 8, fish meal 15, corn steep liquor 5, $KH_2PO_4$ 5, $MgSO_4.7H_2O_2$, $FeSO_4.7H_2O$ 0.1, and the pH of it is adjusted to 6.8.

In one embodiment of the present invention, said flocculation in step (1), could be a thermal flocculation or a flocculant-mediated flocculation.

In one embodiment of the present invention, said filtration in step (1), could be a plate and frame filtration or a membrane filtration.

In one embodiment of the present invention, said centrifugation of fermentation broth in step (1), could be a disk centrifuge, a decanter centrifuge, or a combination of two centrifuges.

In one embodiment of the present invention, said ultrafiltration membrane system in step (2), could be a tubular membrane or wound membranes; the molecular weight cutoff of the ultrafiltration membrane is 10-1000 KDa.

In one embodiment of the present invention, said step (2) is carried out as follows: the fermentation broth supernatant is concentrated 10-20 times by subjecting it to an ultrafiltration membrane with the molecular weight cutoff of 10-1000 KDa, under an operating pressure of 0.1-0.15 MPa.

In one embodiment of the present invention, said ultrafiltration permeate in step (3) is adjusted to pH 5.0-8.5 before pressured into the primary ion exchange column for adsorption.

In one embodiment of the present invention, said primary ion exchange column in step (3) is packed with a weak or strong acid cation exchange resin; the active exchange groups of said resin could be $H^+$, $Na^+$ or $NH_4^+$.

In one embodiment of the present invention, said detergent in step (3) could be deionized water, a dilute acid or alkali aqueous solution; said eluent could be a hydrochloric acid aqueous solution, or an aqueous solution of sodium hydroxide or ammonia.

In one embodiment of the present invention, said secondary ion exchange column in step (3) is packed with a weak or strong base anion exchange resin.

In one embodiment of the present invention, said nanofiltration membrane system in step (4), is a wound membrane, and the nanofiltration membrane has the molecular weight cut-off of 0.1-1.0 KDa.

In one embodiment of the present invention, the operation pressure of said nanofiltration in step (4) is 1.0-1.5 MPa.

In one embodiment of the present invention, said desalting method in step (4), could be intermittent constant volume mode, or continuous constant volume mode, or batch mode, or the combination of one or two modes.

In one embodiment of the present invention, the effluent liquid is concentrated to the concentration of ε-PL and its hydrochloride salt of 5-10%.

In one embodiment of the present invention, said decoloration agent in step (5) could be macroporous resin, or activated carbon.

Advantages of the Present Invention (1) The eluents of ion-exchange chromatograph in the present invention is subjected to deep pretreatment by using ultrafiltration. On the one hand, the clarity of eluents is improved, the contamination of the resin is reduced and the operational life span of the resin is extended; on the other hand, macromolecule impurities, such as proteins and nucleic acids, of the eluents are also removed, and resin adsorption capacity and efficiency are improved;

(2) The present invention employs a two-stage ion exchange for the target ε-PL product by positive and negative adsorption, to obtain the maximum removal of impurities and improve the purification effect of the ion-exchange resin.

(3) A nanofiltration desalting method is used in the present invention to obtain the maximum removal of salt produced by repeatedly adjusting the pH value during the extraction process, and make sure that the ash content of product is controlled at a reasonable level, resulting in significantly improved product purity. Desalting operation unit is introduced into ε-PL extraction process for the first time.

(4) In the present invention, the membrane separation technique (ultrafiltration and nanofiltration) is introduced into the ε-PL separation and extraction process, which has the advantages of high degree of automation, low running cost, the secondary pollution-free, low energy consumption and pollution.

(5) In accordance with the extraction method of the present invention, the recovery and purity of the obtained ε-PL and its hydrochloride salt product is not less than 70% and 95%, respectively.

Preservation of Biomaterials

The *Streptomyces albulus* was deposited in China General Microbiological Culture Collection Center (CGMCC), Institute of Microbiology of Chinese Academy of Science, NO. 1 Beichen West Road, Chaoyang District, Beijing, on Jan. 30, 2015, with the accession number CGMCC No. 10480.

EXAMPLES

Figure 1:
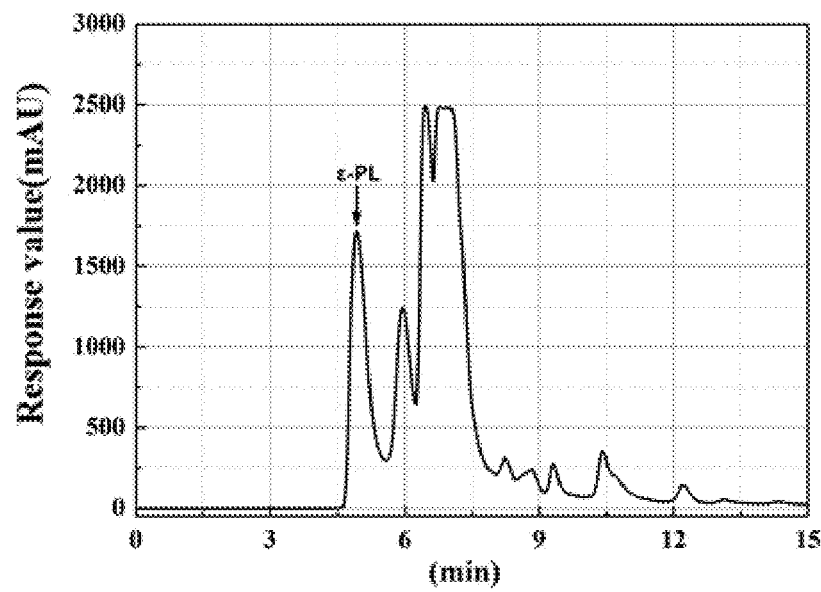
FIG. 1. High-pressure liquid chromatograph of the fermentation broth.
Figure 2:
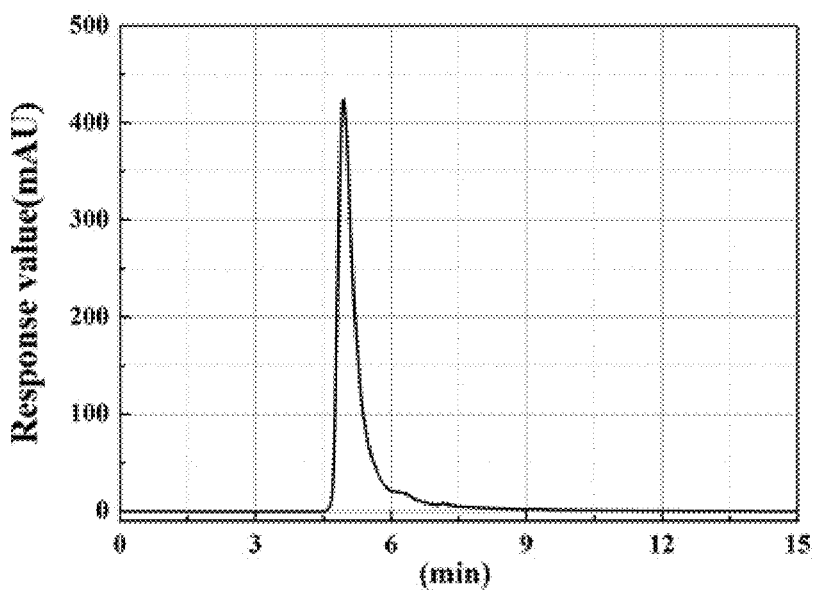
FIG. 2. High pressure liquid chromatograph of the final product of ε-PL obtained by the present invention.
Figure 3:
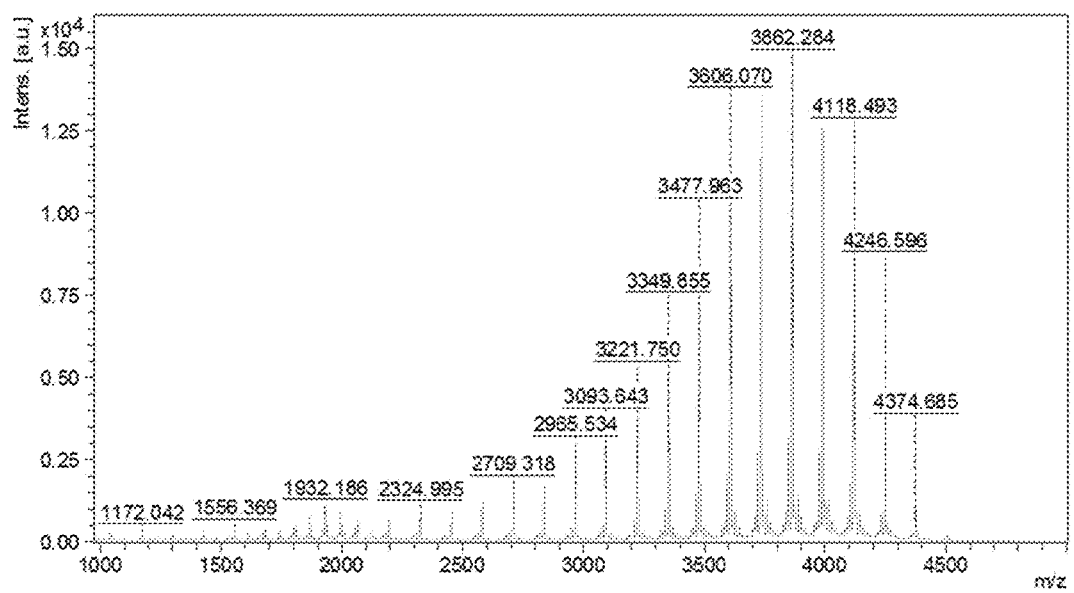
FIG. 3. MALDI-TOF-MS spectra of the final product of ε-PL hydrochloride salt obtained by the present invention.

Materials and Methods:

In the present invention, the ion exchange resin used in the methods is processed by sequential acid washing, alkali washing and acid washing, which is well known by Technical personnel in this field, and the resin is re-usable. In addition, the ultrafiltration membrane and nanofiltration membranes used in the methods is processed by sequential acid washing, alkali washing and acid washing, which is well known by Technical personnel in this field, and the resin is re-usable.

Example 1: Preparation of ε-PL Fermentation Broth

*Streptomyces albulus* CGMCC NO. 10480 was inoculated into the 5 L fermentation tank with 6% inoculum volume of fermentation medium, the medium pH was adjusted to 7.5 with ammonia or NaOH. the fermentation process was controlled with the stirring speed 200-800 rpm, temperature 30° C., ventilation 0.5-2 vvm, dissolved oxygen 30%. When pH drops spontaneously to around 5.0 at the first time, the fermentation pH was maintained at around 5.0 for 10 h; then the pH was regulated to 3.0 and maintained for 24 h, finally the pH was adjusted to around 4.5 and maintained until the end of fermentation. When glycerol or glucose concentration in the fermentation broth drops to less than 10 g·L$^{-1}$, sterilized pure glycerol or 500 g·L$^{-1}$ glucose solution was fed to maintain the concentration of glycerol or glucose at 10 g·L$^{1}$; when NH$_4^+$-N concentration in the fermentation broth dropped to 1 g·L$^{-1}$, the concentration was maintained at 1 g·L$^{-1}$ by feeding the ammonium sulfate solution.

In accordance with the fermentation control method, ε-PL yield could reach 55.4 g·L$^{1}$, dry cell weight was 75.3 g·L$^{1}$, the percentage of wet cells accounted for about 40% of the fermentation broth, through 192 h fed-batch fermentation.

Example 2: Preparation of ε-PL Fermentation Broth

*Streptomyces albulus* CGMCC NO. 10480 was inoculated into the 5 L fermentation tank with 7% inoculum volume of fermentation medium, the medium pH was adjusted to 7.0 with ammonia or NaOH. The fermentation process was controlled with the stirring speed 200-800 rpm, temperature 32° C., ventilation 0.5 vvm, dissolved oxygen 28%. When pH drops spontaneously to around 4.8 at the first time, the fermentation pH was maintained at around 4.8 for 12 h; then the pH was regulated to 3.2 and maintained for 26 h, finally the pH was adjusted to around 4.8 and maintained until the end of fermentation. When glycerol or glucose concentration in the fermentation broth drops to less than 10 g·L$^{-1}$, glycerol or glucose solution was fed to maintain the concentration of glycerol or glucose at 9.5 g·L$^{-1}$; when NH$_4^+$-N concentration in the fermentation broth dropped to 1.0 g·L$^{1}$, the concentration was maintained at 1.2 g·L$^{1}$ by feeding the ammonium sulfate solution.

In accordance with the fermentation control method, ε-PL yield can reach 60 g·L$^{1}$, dry cell weight is 85 g·L$^{1}$, the percentage of wet cells accounted for about 50% of the fermentation broth, through 192 h fed-batch fermentation.

Example 3: Preparation of ε-PL Fermentation Broth

*Streptomyces albulus* CGMCC NO. 10480 was inoculated into the 5 L fermentation tank with 8% inoculum volume of fermentation medium, the medium pH was adjusted to 6.5 with ammonia or NaOH. The fermentation process was controlled with the stirring speed 200-800 rpm, temperature 30° C., ventilation 2 vvm, dissolved oxygen 32%. When pH drops spontaneously to around 4.5 at the first time, the fermentation pH was maintained at around 4.5 for 15 h; then the pH was regulated to 2.8 and maintained for 22 h, finally the pH was adjusted to around 4.2 and maintained until the end of fermentation. When glycerol or glucose concentration in the fermentation broth drops to less than 10 g·L$^{-1}$, glycerol or glucose solution was fed to maintain the concentration of glycerol or glucose at 10.5 g·L$^{-1}$; when NH$_4^+$-N concentration in the fermentation broth dropped to 1.0 g·L$^{-1}$, the concentration was maintained at 0.8 g·L$^{-1}$ by feeding the ammonium sulfate solution.

In accordance with the fermentation control method, ε-PL yield can reach 68.7 g·L$^{-1}$, dry cell weight is 63.8 g·L$^{-1}$, the percentage of wet cells accounted for about 43% of the fermentation broth, through 192 h fed-batch fermentation.

Example 4: Extraction of ε-PL and its Hydrochloride Salt

According to the following method to extract the ε-PL and its hydrochloride salt from the fermentation broth of the example 1:

(1) Fermentation broth of example 1 was diluted by adding 4 times the volume of tap water in the fermentation tank, at room temperature, centrifugation of the fermentation broth diluted by disc centrifuge, a clear fermentation broth supernatant was obtained;

(2) The fermentation broth supernatant was concentrated 10 times by subjecting it to an ultrafiltration membrane with MWCO of 1000 KDa, under the operating pressure of 0.3 MPa. The ultrafiltration permeate was collected.

(3) The ultrafiltration permeate pH was adjusted to 5.0 by 6 M NaOH, and then the ultrafiltration permeate was pressured into the primary ion exchange column, which was loaded with strongly acidic cation resin, with the rate of 1.0 BV·h$^{-1}$ for adsorption. After the saturation of resin, the ion exchange column was washed with deionized water at the rate of 1.0 BV·h$^{-1}$; and then use 1.0 M HCl to desorb the resin with the rate of 1.0 BV·h$^{-1}$. The eluents from the primary ion exchange column was collected, and then the eluents were pressured into a secondary ion exchange column, which was loaded with strongly base anion resin, with the rate of 1.0 BV·h$^{-1}$, and the final eluents was collected;

(4) The ultrafiltration permeate pH was adjust to 5.0 by 6.0 M HCl, and then use nanofiltration membrane MWCO of 100 KDa, under the operating pressure of 1.0 MPa to desalt by adding deionized water with intermittent constant volume mode. After the desalting process, concentrate the eluents 4 times, and then nanofiltration concentrate was collected;

(5) The nanofiltration concentrate was heated to 80° C., and around 1% (w/v) activated carbon was added, the nanofiltration concentrate was decolorized for 20 min under stirring condition, the activated carbon was removed by filtration and the decolorated liquid was collected;

(6) The decolorated liquid obtained from the step (5) was concentrated to ε-polylysine content of around 10% by evaporation;

(7) The concentrate obtained from the step (6) was dried by spray drying, the ε-polylysine and its hydrochloride salt product was collected.

According to the above extraction process, the total content of ε-PL and its hydrochloride in the product was 95.12%, that is, the purity of ε-PL and its hydrochloride was 95.12%. The yield of ε-PL and its hydrochloride was 72.3%.

With the same method, the fermentation broth obtained by the examples 2 and 3 was extracted, and the purity of the ε-PL and its hydrochloride was 96.15% and 95.38%, respectively, and the yield reached 71.2% and 70.6%, respectively.

Example 5: Extraction of ε-PL and its Hydrochloride Salt

According to the following method to extract the ε-PL and its hydrochloride salt from the fermentation broth of the example 1:

(1) The fermentation broth of example 1 was flocculated by adding a certain concentration of flocculant in the fermentation tank, at room temperature, the fermentation broth was filtrated by plate and frame filter, a clear fermentation broth supernatant was obtained;

(2) The fermentation broth supernatant was concentrated 5 times by subjecting it to an ultrafiltration membrane with MWCO of 10 KDa, under the operating pressure of 0.15 MPa. and the ultrafiltration permeate was collected.

(3) The ultrafiltration permeate pH was adjusted to 8.5 by 6 M NaOH, and then the ultrafiltration permeate was pressured into the primary ion exchange column, which was loaded with macroporous weak acid cation resin, with the rate of 10 BV·h$^{-1}$ for adsorption. After the saturation of resin, the ion exchange column was washed with deionized water at the rate of 10 BV·h$^{-1}$; and then use 1 M NaOH to desorb the resin with the rate of 10 BV·h$^{-1}$. The eluents from the primary ion exchange column was collected, and then the eluents were pressured into a secondary ion exchange column, which was loaded with macroporous weak basic anion resin, with the rate of 10 BV·h$^{-1}$, and the final eluents was collected;

(4) The ultrafiltration permeate pH was adjust to 8.0 by 6 M HCl, and then use nanofiltration membrane MWCO of 1000 KDa, under the operating pressure of 1.5 MPa to desalt by adding deionized water with continuous constant volume mode. After the desalting process, concentrate the eluents 2 times, and then nanofiltration concentrate was collected;

(5) The nanofiltration concentrate was heated to 100° C., and around 1.5% (m/v) activated carbon was added, the nanofiltration concentrate was decolorized for 30 min under stirring condition, the activated carbon was removed by filtration and the decolorated liquid was collected;

(6) The decolorated liquid obtained from the step (5) was concentrated to ε-polylysine content of around 30% by evaporation;

(7) The concentrate obtained from the step (6) was dried by spray drying, the ε-polylysine and its hydrochloride salt product was collected.

According to the above extraction process, the purity of ε-PL and its hydrochloride was 96.82%. and the yield of ε-PL and its hydrochloride was 70.5%.

With the same method, the fermentation broth obtained by the examples 2 and 3 was extracted, and the purity of the ε-PL and its hydrochloride was 97.21% and 96.85%, respectively, and the yield reached 71.5% and 73.6% respectively.

Example 6: Extraction of ε-PL and its Hydrochloride Salt

According to the following method to extract the ε-PL and its hydrochloride salt from the fermentation broth of the example 1:

(1) Fermentation broth of example 1 was diluted by adding 8 times the volume of tap water in the fermentation tank, at room temperature, centrifugation of the fermentation broth diluted by disc centrifuge, a clear fermentation broth supernatant was obtained;

(2) The fermentation broth supernatant was concentrated 20 times by subjecting it to an ultrafiltration membrane with MWCO of 800 KDa, under the operating pressure of 0.1 MPa. and the ultrafiltration permeate was collected.

(3) The ultrafiltration permeate pH was adjusted to 7.0 by 6 M NaOH, and then the ultrafiltration permeate was pressured into the primary ion exchange column, which was loaded with macroporous weak acid cation resin, with the rate of 5 BV·h$^{-1}$ for adsorption. After the saturation of resin, the ion exchange column was washed with deionized water at the rate of 5 BV·h$^{-1}$; and then use 1 M ammonia to desorb the resin with the rate of 5 BV·h$^{-1}$. The eluents from the primary ion exchange column was collected, and then the eluents were pressured into a secondary ion exchange column, which was loaded with strongly base anion resin, with the rate of 5 BV·h$^{-1}$, and the final eluents were collected;

(4) The ultrafiltration permeate pH was adjust to 8.5 by 6 M HCl, and then use nanofiltration membrane MWCO of 500 KDa, under the operating pressure of 1.2 MPa to desalt by adding deionized water with One-time addition mode. After the desalting process, concentrate the eluents 2 times, and then nanofiltration concentrate was collected;

(5) The nanofiltration concentrate was heated to 90° C., and around 2% (m/v) activated carbon was added, the nanofiltration concentrate was decolorized for 15 min under stirring condition, the activated carbon was removed by filtration and the decolorated liquid was collected;

(6) The decolorated liquid obtained from the step (5) was concentrated to ε-polylysine content of around 20% by evaporation;

(7) The concentrate obtained from the step (6) was dried by spray drying, the ε-polylysine and its hydrochloride salt product was collected.

According to the above extraction process, the purity of ε-PL and its hydrochloride was 97.10%. The yield of ε-PL and its hydrochloride was 75.2%.

With the same method, the fermentation broth obtained by the examples 2 and 3 was extracted, and the purity of the ε-PL and its hydrochloride was 95.13% and 96.51%, respectively, and the yield reached 70.2% and 74.1% respectively.

Contrast 1:

The fermentation broth obtained from Example 1 was extracted by using the method described in CN201110053004.2, and the following was a specific implementation process.

The pH of the fermentation broth was adjusted to 5.0 with 2 mol/L hydrochloric acid in the acidification tank, and the acidified solution was heated to 100° C., and was incubated for 10 minutes. The acidified solution was cooled down to room temperature, then it was filtered through the plate frame to get clear filtrate. 6 mol/L sodium hydroxide solution was added to the clear filtrate, the pH of filtrate was adjusted to 7.2 to obtain pretreatment liquid.

The pretreatment liquid was pumped into the adsorption column filled with macroporous strong acidic ion exchange resin (D001) with height to diameter ratio of 10:1, and the adsorption process should be controlled at a rate of 4 ml/min (about 4 BV·h$^{-1}$), until the resin saturated. Wash the saturated resin with 5 column volumes of deionized water at a flow rate of 5 ml/min (about 5 BV·h$^{-1}$). 1 mol/L acetic acid solution was used to desorb the resin, and the flow rate was controlled at 1 ml/min (about 1 BV·h$^{-1}$). Desorbing solution containing ε-PL was collected at different retention times by Itzhaki methods or HPLC. 2.0% (w/w) of activated carbon was added to the desorbing solution containing ε-PL, and the mixture was heated to 100° C., and was stirred for 60 minutes for decolorization, and then cooled it down to room temperature. Finally, the mixture was filtered to yield a decolorized solution.

Decolorized solution containing ε-PL was forced into an evaporation concentration device to conduct cyclic concentration, When the ε-PL content reached 20% (w/w), the concentration process was stopped.

ε-PL product can be obtained by freeze-drying the concentrated liquid. The recovery and purity of ε-PL and its hydrochloride salt were 62.1% and 52.6%, respectively.

Contrast 2:

Omit step (2) in Example 4, other conditions were in consistent with Example 4, and treated the same fermentation broth as in Example 1. The results show that the purity and the yield of ε-PL and its hydrochloride salt obtained by this method are 92.10% and 77.2%, respectively.

Contrast 3:

The step (3) in Example 4 were adjusted, and other treatment conditions were in consistent with Example 4, and treated the same fermentation broth as in Example 1.

The specific adjusted step (3) was that the pH of the permeate was adjusted to 7.0 by 6 M NaOH, then the permeate was forced into the primary ion exchange column packed with macroporous weak acidic cation exchange resin at the rate of 5 $BV·h^{-1}$ for ion exchange; when the resin was saturated, it was washed by deionized water at the rate of 5 $BV·h^{-1}$; after washing, the resin was eluted with 1 M ammonia water at the rate of 5 $BV·h^{-1}$, and the eluents were collected.

The results show that the purity and the yield of ε-PL and its hydrochloride salt are 93.40% and 80.31%, respectively.

Contrast 4:

Omit step (4) in Example 4, and other conditions were in consistent with Example 4, and treated the same fermentation broth as in Example 1. The results show that the purity and the yield of ε-PL and its hydrochloride salt obtained by this method are 73.65% and 76.86%, respectively.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A method for extraction of ε-polylysine (ε-PL) and its hydrochloride salt from a fermentation broth, comprising the following steps:
   (1) solid-liquid separating of the fermentation broth: after flocculation or dilution, filtrating or centrifugating the fermentation broth to remove mycelia and water-insoluble impurities, and obtaining a clear fermentation broth supernatant;
   (2) ultrafiltrating: using an ultrafiltration membrane system to remove the water-soluble macromolecular impurities and water-insoluble impurities in the fermentation broth supernatant, and collecting ultrafiltration permeate;
   (3) ion-exchanging: pressuring the ultrafiltration permeate into a primary ion exchange column for adsorption until resin is saturated; using a detergent to remove impurities, and using an elution reagent to desorb; collecting eluents from the primary ion exchange column, and then forcing into a secondary ion exchange column, and collecting a final effluent liquid;
   (4) nanofiltrating: using a nanofiltration membrane system to desalt and concentrate the final effluent liquid obtained from the step (3), and collecting a nanofiltration concentrate;
   (5) bleaching: decolorating collected nanofiltration concentrate to obtain a decolorated liquid;
   (6) concentrating: concentrating the decolorated liquid obtained from the step (5) to obtain a concentrate of a ε-polylysine content of 10-30% as a percent weight/volume;
   (7) drying: drying the concentrate obtained from the step (6) to obtain ε-polylysine and its hydrochloride salt product;
   wherein the ultrafiltration membrane system in step (2) is a tubular membrane or a wound membrane; wherein the molecular weight cutoff of an ultrafiltration membrane in the ultrafiltration membrane system is 50-1000 KDa;
   wherein the primary ion exchange column in step (3) is a weak or strong acid cation exchange resin, and the secondary ion exchange column in step (3) is a weak or strong base anion exchange resin;
   wherein the fermentation broth is obtained by fermentation of *Streptomyces albulus* CGMCC NO. 10480.

2. The method of claim 1, wherein the fermentation broth contains over 50 $g·L^{-1}$ ε-PL and over 60 $g·L^{-1}$ dry-weight cell.

3. The method of claim 1, wherein the fermentation broth is prepared by the following steps: inoculating *Streptomyces albulus* CGMCC NO. 10480 into a fermentation medium with 6%-8% inoculum volume, controlling fermentation process with a stirring speed 200-800 rpm, a temperature between 28-32° C., ventilation 0.5-2 volume/culture volume/min (vvm), and dissolved oxygen at 28-32%; when pH drops spontaneously to 4.5-5.2 at a first time, maintaining a fermentation pH at 4.8-5.2 for 10-15 h, and adjusting the fermentation pH to 2.8-3.2 and maintaining the fermentation pH for 22-26 h, and finally adjusting the fermentation pH to 4.2-4.8 and maintaining the fermentation pH until; when glycerol or glucose concentration in the fermentation broth drops to less than 10 $g·L^{-1}$, feeding glycerol or glucose solution to maintain the concentration of glycerol or glucose at 9.5-10.5 $g·L^{-1}$; when $NH_4^+$—N concentration in the fermentation broth drops to 1 $g·L^{-1}$ or less, maintaining the $NH_4^+$—N concentration at 0.8-1.2 $g·L^{-1}$ by feeding ammonium sulfate solution.

4. The method of claim 3, wherein the fermentation medium contains the following components: glucose or glycerol, $(NH_4)_2SO_4$, fish meal, corn steep liquor, $KH_2PO_4$, $MgSO_4.7H_2O_2$, $FeSO_4.7H_2O$, and a pH is at 6.8.

5. The method of claim 1, wherein the nanofiltration membrane system in step (4), is a wound membrane, and the nanofiltration membrane has a molecular weight cutoff of 0.1-1.0 KDa.

6. The method of claim 1, wherein an operation pressure of said nanofiltration in step (4) is 1.0-1.5 MPa.

* * * * *